United States Patent [19]

Cantatore et al.

[11] Patent Number: 5,047,531

[45] Date of Patent: Sep. 10, 1991

[54] PIPERIDINE-TRIAZINE COMPOUNDS FOR USE AS STABILIZERS FOR ORGANIC MATERIALS

[75] Inventors: Giuseppe Cantatore, Bitonto; Graziano Vignali, Sasso Marconi, both of Italy

[73] Assignee: Ciba-Geigy Corporation, Ardsley, N.Y.

[21] Appl. No.: 389,152

[22] Filed: Aug. 2, 1989

[30] Foreign Application Priority Data

Aug. 4, 1988 [IT] Italy .............................. 21644 A/88

[51] Int. Cl.[5] .................. C07D 251/50; C07D 251/70; C08K 5/34; C08L 25/06

[52] U.S. Cl. .................................... 544/198; 540/554; 540/575; 540/598; 544/113; 544/60; 544/209; 430/270; 524/96; 524/98; 524/100

[58] Field of Search ................. 544/198, 113, 209, 60; 540/575, 598, 554

[56] References Cited

U.S. PATENT DOCUMENTS

| | | | |
|---|---|---|---|
| 4,108,829 | 8/1978 | Cassandrini et al. | 544/198 |
| 4,288,593 | 9/1981 | Rody | 544/198 |
| 4,335,242 | 6/1982 | Wiezer et al. | 544/209 |
| 4,376,836 | 3/1983 | Wiezer et al. | 544/198 |
| 4,409,348 | 10/1983 | Wiezer et al. | 544/209 |
| 4,433,145 | 2/1984 | Wiezer et al. | 544/198 |
| 4,468,488 | 8/1984 | Minagawa et al. | 544/209 |
| 4,492,791 | 1/1985 | Orban et al. | 544/209 |
| 4,533,688 | 8/1985 | Toda et al. | 544/198 |

FOREIGN PATENT DOCUMENTS

| | | | |
|---|---|---|---|
| 0094048 | 5/1983 | European Pat. Off. | |
| 0112690 | 7/1984 | European Pat. Off. | |
| 0176106 | 4/1986 | European Pat. Off. | 544/198 |

*Primary Examiner*—Johann Richter
*Attorney, Agent, or Firm*—Luther A. R. Hall

[57] ABSTRACT

Piperidine-triazine compounds of the general formula (I)

(I)

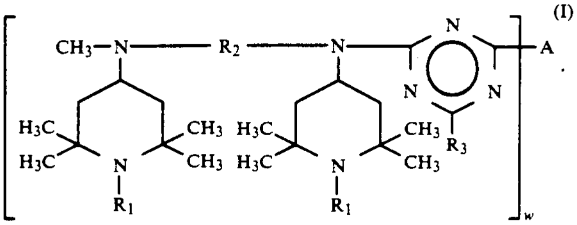

in which $R_1$ is e.g. hydrogen or methyl, $R_2$ is e.g. $C_2$-$C_6$alkylene, $R_3$ is e.g. a group

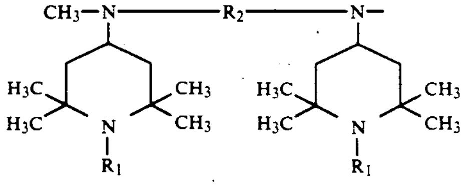

and w is e.g. 2 or 3, if w is 2, A is e.g.

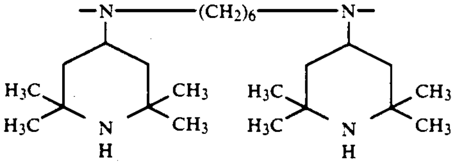

and if w is 3, A is e.g.

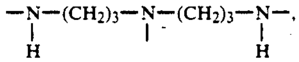

can be used as light stabilizers, heat stabilizers and oxidation stabilizers for organic materials, in particular synthetic polymers.

8 Claims, No Drawings

PIPERIDINE-TRIAZINE COMPOUNDS FOR USE AS STABILIZERS FOR ORGANIC MATERIALS

The present invention relates to novel piperidine-triazine compounds, to their use as light stabilizers, heat stabilizers and oxidation stabilizers for organic materials, in particular synthetic polymers, and to the organic materials thus stabilized.

It is known that synthetic polymers undergo a photo-oxidative degradation when they are exposed to sunlight or other sources of ultraviolet light in the presence of oxygen.

When they are used in practice, it is therefore necessary to add to them suitable light stabilizers, such as certain benzophenone or benzotriazole derivatives, nickel complexes, substituted benzoic acid esters, alkylidenemalonates, cyanoacrylates, aromatic oxamides or sterically hindered amines.

Some triazine derivatives of 2,2,6,6-tetramethyl-4-piperidylamine and their use as stabilizers for synthetic polymers have been described in U.S. Pat. No. 4,108,829, 4,288,593, 4,376,836, 4,433,145 and 4,533,688 and in European Pat. No. 176,106.

In particular, the present invention relates to novel compounds of the general formula (I)

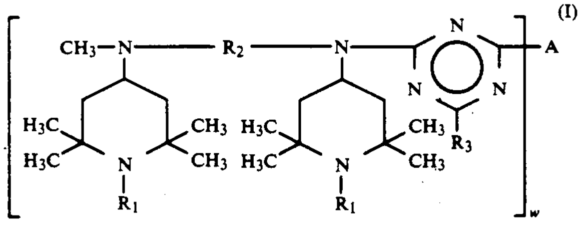
(I)

in which $R_1$ is hydrogen, $C_1$-$C_8$alkyl, O., OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl, $C_1$-$C_8$acyl or $C_2$-$C_4$alkyl substituted in the 2-, 3- or 4-position by OH, $R_2$ is $C_2$-$C_{12}$alkylene, $R_3$ is a group of the formula (II)

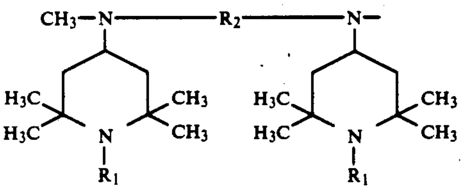
(II)

with $R_1$ and $R_2$ being as defined above, or $R_3$ is a group $—OR_4$, $—SR_4$ or

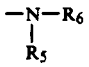

in which $R_4$ is $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl, $C_7$-$C_9$-phenylalkyl which is unsubstituted or mono-, di- or tri-substituted on the phenyl by $C_1$-$C_4$alkyl, or a group of the formula (III)

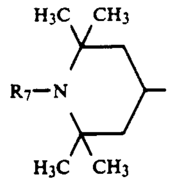
(III)

where $R_7$ has any of the meanings given for $R_1$, $R_5$ and $R_6$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, C7-C9-phenylalkyl which is unsubstituted or mono-, di- or tri-substituted on the phenyl by $C_1$-$C_4$alkyl, $C_2$-$C_4$alkyl substituted in the 2-, 3- or 4- position by OH, by $C_1$-$C_8$alkoxy or by di-($C_1$-$C_4$alkyl)-amino, $C_3$-$C_{18}$-alkenyl, tetrahydrofurfuryl or a group of the formula (III), or $R_5$ and $R_6$, together with the nitrogen atom to which they are linked, form part of a 5-membered to 7-membered heterocyclic ring, and w is an integer from 2 to 6, and if w is 2, A is one of the groups of the formula (IVa)-(IVd)

$—O—R_8—O—$, (IVa)

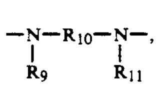
(IVb)

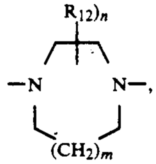
(IVc)

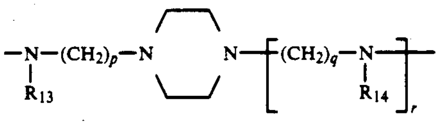
(IVd)

in which $R_8$ is $C_2$-$C_{12}$alkylene, cyclohexylene, cyclohexylenedimethylene, methylenedicyclohecxylene, ($C_2$-$C_6$alkylidene)-dicyclohexylene, phenylene, ($C_2$-$C_6$alkylidene)-iiphenylene, xylylene or $C_4$-$C_{12}$alkylene interrupted by 1, 2 or 3 oxygen atoms, $R_9$ and $R_{11}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, or a group of the formula (III), $R_{10}$ is as defined above for $R_8$ or $C_4$-$C_{12}$alkylene interrupted by 1 or 2 groups N-$R_{15}$ where $R_{15}$ has any of the meanings given for $R_9$ and $R_{11}$, or is one of the groups of the formula (Va)-(Vd)

| $—COR_{16}$, | $—COOR_{17}$, | $—COCOOR_{17}$, | $—SO_2R_{18}$ |
|---|---|---|---|
| (Va) | (Vb) | (Vc) | (Vd) |

where $R_{16}$ is hydrogen, $C_1$-$C_{18}$alkyl, $C_5$-$C_{12}$cycloalkyl which is unsubstituted or mono-, di- or tri-substituted by $C_1$-$C_4$alkyl, $C_2$-$C_{18}$alkenyl, phenyl which is unsubstituted or mono-, di- or tri-substituted by $C_1$-$C_4$alkyl and/or an OH group, $C_7$-$C_9$phenylalkyl which is unsubstituted or mono-, di- or tri-substituted on the phenyl by $C_1$-$C_4$alkyl and/or an OH group, $R_{17}$ is $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl or a group of the formula (III), $R_{18}$ is $C_1$-$C_{18}$alkyl or phenyl which is unsubstituted or mono-, di- or tri-substituted by $C_1$-$C_4$alkyl, m is zero or 1, $R_{12}$ is hydrogen or methyl, n is zero, 1, 2, 3 or 4, $R_{13}$ and $R_{14}$ which are identical or different are as defined above for $R_9$ and $R_{11}$, p and q which can be identical or different are integers from 2 to 6 and r is zero or 1, and, if w is 3, A is one of the groups of the formula (VIa)-(VIc)

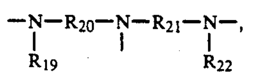

(VIa)

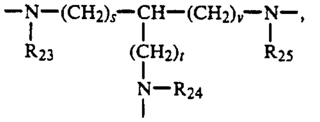

(VIb)

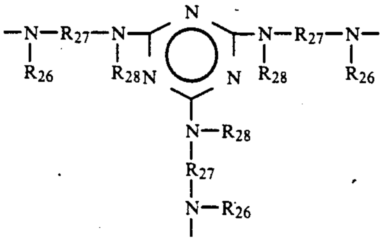

(VIc)

in which $R_{19}$, $R_{22}$, $R_{23}$, $R_{24}$, $R_{25}$, $R_{26}$ and $R_{28}$ which can be identical or different are as defined above for $R_9$ and $R_{11}$; $R_{20}$ and $R_{21}$ which can be identical or different are $C_2$-$C_{12}$alkylene or $C_4$-$C_{12}$alkylene interrupted by a group N-$R_{29}$ being defined as above for $R_{15}$, s and v which can be identical or different are integers from 2 to 6, t is zero or 1 and $R_{27}$ is $C_2$-$C_{12}$alkylene, and if w is 4, 5 or 6, A is additionally a group of the formula (VIII)

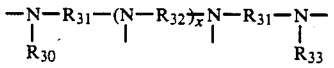

(VII)

in which $R_{30}$ and $R_{33}$ which can be identical or different are as define above for $R_9$ and $R_{11}$; $R_{31}$ and $R_{32}$ which can be identical or different are $C_2$-$C_{12}$alkylene and x is 1, 2 or 3, and, if w is 4, A is also one of the groups of the formula (VIIIa)-(VIIIc)

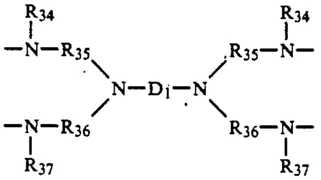

(VIIIa)

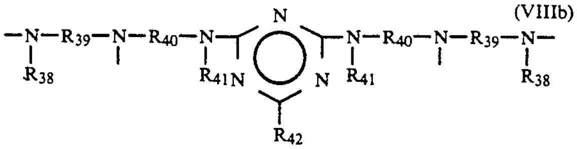

(VIIIb)

-continued

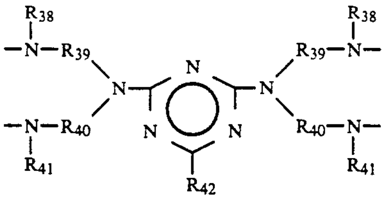

(VIIIc)

in which $R_{34}$, $R_{37}$, $R_{38}$ and $R_{41}$ which can be identical or different are as defined above for $R_9$ and $R_{11}$; $R_{35}$, $R_{36}$, $R_{39}$ and $R_{40}$ which can be identical or different are $C_2$-$C_{12}$alkylene, $D_1$ is $C_2$-$C_{12}$alkylene, 2-hydroxytrimethylene, $-CH_2CO-$, xylylene or one of the groups of the formula (IXa) or (IXb)

$-COR_{43}CO-$ (IXa) $-COOR_{44}OOC-$ (IXb)

in which $R_{43}$ is a direct bond, $C_1$-$C_{12}$alkylene, cyclohexylene or phenylene, $R_{44}$ is as defined above for $R_8$ and $R_{42}$ is as defined above for $R_3$, and, if w is 6, A is also one of the groups of the formula (Xa)-(Xc)

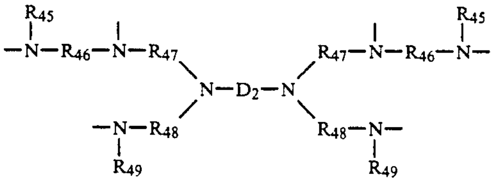

(Xa)

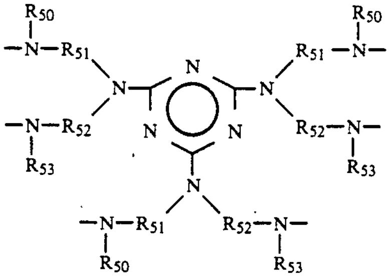

(Xb)

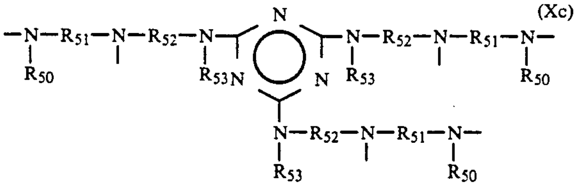

(Xc)

in which $R_{45}$, $R_{49}$, $R_{50}$ and $R_{53}$ which can be identical or different are as defined above for $R_9$ and $R_{11}$; $R_{46}$, $R_{47}$, $R_{48}$, $R_{51}$ and $R_{52}$ which can be identical or different are $C_2$-$C_{12}$alkylene and $D_2$ is as defined above for $D_1$.

Representative examples of $C_1$-$C_8$alkyl $R_1$ and $R_7$ are methyl, ethyl, propyl, butyl, isobutyl, pentyl, hexyl, heptyl and octyl. $C_1$-$C_4$alkyl, in particular methyl, is preferred.

Examples of $C_1$-$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of OH-substituted $C_2$-$C_4$alkyl are 2-hydroxyethyl, 2-hydroxypropyl, 3-hydroxypropyl, 2- hydroxybutyl and 4-hydroxybutyl. 2-Hydroxyethyl is preferred.

Examples of $C_2$–$C_4$alkyl substituted by $C_1$–$C_8$alkoxy, preferably $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di-($C_1$–$C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$–$C_{18}$alkoxy $R_1$ and $R_7$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy or octoxy, are preferred.

Examples of unsubstituted or substituted $C_5$–$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl is preferred.

Representative examples of $C_5$–$C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are vinyl, allyl, 2-methylallyl, hexenyl, decenyl, undecenyl, heptadecenyl and oleyl. Allyl is one of the preferred definitions of $R_1$ and $R_7$. In alkenyl $R_1$, $R_4$–$R_7$ and $R_{17}$, the carbon atom in the 1-position is preferably a saturated carbon atom.

Examples of substituted phenyl are methylphenyl, dimethylphenyl, trimethylphenyl, t-butylphenyl, di-t-butylphenyl, hydroxyphenyl and 3,5-di-t-butyl-4-hydroxyphenyl.

Examples of phenylalkyl which is unsubstituted or substituted on the phenyl are benzyl, methylbenzyl, dimethylbenzyl, t-butylbenzyl, 2-phenylethyl and 2-(3,5-di-t-butyl-4-hydroxyphenyl)ethyl.

Acyl $R_1$ and $R_7$ having up to 8 carbon atoms can be an aliphatic or aromatic group. Representative examples are formyl, acetyl, propionyl, butyryl, pentanoyl, hexanoyl, octanoyl, benzoyl, acryloyl and crotonyl. $C_1$–$C_8$alkanoyl, $C_3$–$C_8$alkenoyl and benzoyl are preferred. Acetyl is particularly preferred.

Representative examples of $R_5$ and $R_6$ which, together with the nitrogen atom to which they are linked, form part of a 5-membered to 7-membered heterocyclic ring preferably containing a further heteroatom, for example nitrogen or oxygen, are 1-pyrrolidyl, 1-piperidyl, 4-morpholinyl, 4-methyl-1-piperazinyl, 1-hexahydroazepinyl, 5,5,7-trimethyl-1-homopiperazinyl and 4,5,5,7-tetramethyl-1-homopiperazinyl. 4-Morpholinyl is particularly preferred.

Examples of alkylene having up to 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene. $R_2$, $R_{10}$, $R_{20}$, $R_{21}$, $R_{31}$ and $R_{32}$ are preferably $C_2$–$C_6$alkylene.

Examples of $C_4$–$C_{12}$alkylene interrupted by 1, 2 or 3 oxygen atoms are 3-oxapentane-1,5-diyl, 3,6-dioxaoctane-1,8-diyl and 3,6,9-trioxaundecane-1,11-diyl.

Representative examples of $C_4$–$C_{12}$alkylene $R_{10}$ interrupted by 1 or 2 groups

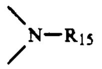

are the groups.

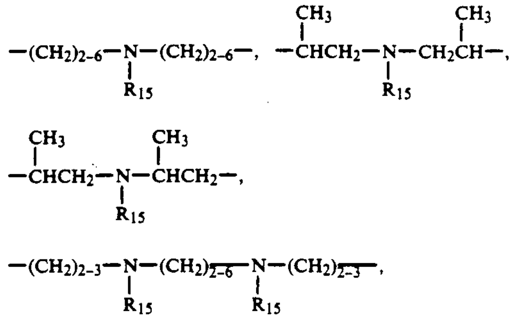

in which $R_{15}$ has any of the meanings given above, preferably hydrogen, methyl or ($C_2$–$C_4$alkoxy)-carbonyl.

Representative examples of alkylene $R_{20}$ and $R_{21}$ interrupted by a group

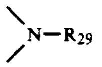

are the groups

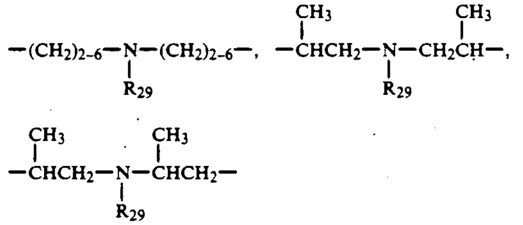

in which $R_{29}$ has any of the meanings given above, preferably hydrogen, methyl or ($C_2$–$C_4$alkoxy)-carbonyl.

An example of ($C_2$–$C_6$alkylidene)-dicyclohexylene is isopropylidenedicyclohexylene, and an example of ($C_2$–$C_6$alkylidene)-dephenylene is isopropylidenediphenylene.

$R_1$ is preferably hydrogen, $C_1$–$C_4$alkyl, OH, $C_6$–$C_{12}$alkoxy, $C_5$–$C_8$-cycloalkoxy, allyl, benzyl, acetyl or 2-hydroxyethyl, in particular hydrogen or methyl.

Those compounds of the formula (I) are preferred in which $R_2$ is $C_2$–$C_{10}$-alkylene, $R_3$ is a group of the formula (II), a group $—OR_4$, $—SR_4$ or

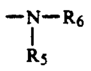

in which $R_4$ is $C_1$–$C_{12}$alkyl, $C_5$–$C_8$cycloalkyl which is unsubstituted or mono-, di- or tri-substituted by $C_1$–$C_4$alkyl, $C_3$–$C_{12}$alkenyl, phenyl, benzyl or a group of the formula (III), $R_5$ and $R_6$ which can be identical or different are hydrogen, $C_1$–$C_{18}$alkyl, $C_5$–$C_8$cycloalkyl which is unsubstituted or mono-, di- or tri-substituted by $C_1$–$C_4$alkyl, benzyl, $C_2$–$C_3$alkyl substituted in the 2- or 3-position by OH, by $C_1$–$C_4$-alkoxy or by di-($C_1$–$C$-

4alkyl)-amino, allyl, oleyl, tetrahydrofurfuryl or a group of the formula (III), or the groups

is 1-pyrrolidyl, 1-piperidyl, 4-morpholinyl or 1-hexahydroazepinyl, w is an integer from 2 to 6 and, if w is 2, A is one of the groups of formula (IVa)-(IVd) in which $R_8$ is $C_2$–$C_{10}$alkylene, cyclohexylene, cyclohexylenedimethylene, methylenedicyclohexylene, isopropylidenedicyclohexylene, isopropylidenediphenylene or $C_4$–$C_{10}$alkylene interrupted by 1, 2 or 3 oxygen atoms, $R_9$ and $R_{11}$ which can be identical or different are hydrogen, $C_1$–$C_{12}$alkyl, $C_5$–$C_8$cycloalkyl which is unsubstituted or mono-, di- or trisubstituted by $C_1$–$C_4$alkyl, benzyl or a group of the formula (III), $R_{10}$ is as defined above for $R_8$ or is $C_4$–$C_{12}$alkylene interrupted by 1 or 2 groups

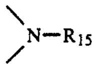

where $R_{15}$ has any of the meanings given for $R_9$ and $R_{11}$, or is one or the groups of the formula (Va)-(Vd) in which $R_{16}$ is hydrogen, $C_1$–$C_{17}$alkyl, $C_5$–$C_8$cycloalkyl which is unsubstituted or mono-, di-or tri-substituted by $C_1$–$C_4$alkyl, $C_2$–$C_{17}$alkenyl, phenyl which is unsubstituted or mono-, di- or tri-substituted by $C_1$–$C_4$alkyl and/or an OH group, $C_7$–$C_8$phenylalkyl which is unsubstituted or mono-, di- or trisubstituted on the phenyl by $C_1$–$C_4$alkyl and/or an OH group, $R_{17}$ is $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (III) and $R_{18}$ is $C_1$–$C_{12}$alkyl, phenyl or tolyl, m is zero or 1, $R_{12}$ is hydrogen or methyl, n is zero, 1, 2, 3 or 4, $R_{13}$ and $R_{14}$ which can be identical or different are as defined above for $R_9$ and $R_{11}$, p and q which can be identical or different are 2 or 3 and r is zero or 1, and, if w is 3, A is one of the groups of the formula (VIa)-(VIc) in which $R_{19}$, $R_{22}$, $R_{23}$, $R_{24}$, $R_{25}$, $R_{26}$ and $R_{28}$ which can be identical or different are as defined above for $R_9$ and $R_{11}$; $R_{20}$ and $R_{21}$ which can be identical or different are $C_2$–$C_{10}$alkylene or $C_4$–$C_{12}$alkylene which is interrupted by a group

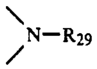

with $R_{29}$ being as defined above for $R_{15}$, s and v which can be identical or different are integers from 2 to 6, t is zero or 1 and $R_{27}$ is $C_2$–$C_{10}$alkylene, and, if w is 4, 5 or 6, A is a group of the formula (VII) in which $R_{30}$ and $R_{33}$ which can be identical or different are as defined above for $R_9$ and $R_{11}$; $R_{31}$ and $R_{32}$ which can be identical or different are $C_2$–$C_{10}$alkylene and x is 1, 2 or 3, and, if w is 4, A can also be one of the groups of the formula (VIIIa)-(VIIIc) in which $R_{34}$, $R_{37}$, $R_{38}$ and $R_{41}$ which can be identical or different are as defined above for $R_9$ and $R_{11}$; $R_{35}$, $R_{36}$, $R_{39}$ and $R_{40}$ which can be identical or different are $C_2$–$C_{10}$alkylene, $D_1$ is $C_2$–$C_{10}$alkylene, 2-hydroxytrimethylene, —$CH_2CO$—, xylylene or one of the groups of the formula (IXa) or (IXb) in which $R_{43}$ is a direct bond or $C_1$–$C_{10}$alkylene, $R_{44}$ is as defined above for $R_8$ and $R_{42}$ is as defined above for $R_3$ and, if w is 6, A is also one of the groups of the formula (Xa)-(Xc) in which $R_{45}$, $R_{49}$, $R_{50}$ and $R_{53}$ which can be identical or different are as defined above for $R_9$ and $R_{11}$; $R_{46}$, $R_{47}$, $R_{48}$, $R_{51}$ and $R_{52}$ which can be identical or different are $C_2$–$C_{10}$alkylene and $D_2$ is as defined above for $D_1$.

Those compounds of the formula (1) are particularly preferred in which $R_2$ is $C_2$–$C_8$alkylene, $R_3$ is a group of the formula (II), a group —$OR_4$ or

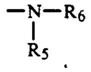

in which $R_4$ is $C_1$–$C_8$alkyl, cyclohexyl which is unsubstituted or mono-, di- or tri-substituted by $C_1$–$C_4$alkyl, allyl, undecenyl, phenyl, benzyl or a group of the formula (III), $R_5$ and $R_6$ which can be identical or different are hydrogen, $C_1$–$C_{12}$alkyl, cyclohexyl which is unsubstituted or mono-, di- or tri-substituted by $C_1$–$C_4$alkyl, benzyl, $C_2$–$C_3$alkyl substituted in the 2- or 3-position by OH, by methoxy, by ethoxy, by dimethylamino or by diethylamino, allyl tetrahydrofurfuryl or a group of the formula (III), or the group

is 4-morpholinyl, w is an integer from 2 to 6 and, if 1 is 2, A is one of the groups of the formula (IVb)-(IVd) in which $R_9$ and $R_{11}$ which can be identical or different are hydrogen, $C_1$–$C_8$alkyl, cyclohexyl which is unsubstituted or mono-, di- or trisubstituted by $C_1$–$C_4$alkyl, benzyl or a group of the formula (III), $R_{10}$ is $C_2$–$C_8$alkylene, cyclohexylenedimethylene, methylenedicyclohexylene, $C_4$–$C_8$alkylene interrupted by 1 or 2 oxygen atoms or $C_4$–$C_{12}$alkylene interrupted by 1 or 2 groups

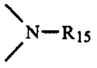

where $R_{15}$ has any of the meanings given for $R_9$ and $R_{11}$, or is one of the groups of the formula (Va)-(Vc) in which $R_{16}$ is $C_1$–$C_{17}$alkyl, cyclohexyl which is unsubstituted or mono-, di- or tri-substituted by $C_1$–$C_4$alkyl, $C_2$–$C_{10}$alkenyl, phenyl, 3,5-di-t-butyl-4-hydroxyphenyl, benzyl or 2-(3,5-di-t-butyl-4-hydroxyphenyl)ethyl, $R_{17}$ is $C_1$–$C_{18}$alkyl, cyclohexyl which is unsubstituted or mono-, di- or tri-substituted by $C_1$–$C_4$alkyl, allyl, undecenyl, oleyl or a group of the formula (III), m is zero or 1, $R_{12}$ is hydrogen or methyl, n is zero, 1, 2 or 3, $R_{13}$ and $R_{14}$ which can be identical or different are as defined above for $R_9$ and $R_{11}$, p and q which can be identical or different are 2 or 3 and r is zero or 1, and, if w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$–$C_8$ alkylene and $R_{20}$ is also $C_4$–$C_{12}$ alkylene interrupted by a group

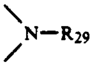

with $R_{29}$ being as defined above for $R_{15}$, and, if w is 4, 5 or 6, A is a group of the formula (VII) in which $R_{30}$ and $R_{33}$ which can be identical or different are as defined above for $R_9$ and $R_{11}$; $R_{31}$ and $R_{32}$ which can be identical or different are $C_2$–$C_8$alkylene and x is 1, 2 or 3, and, if w is 4, A is also a group of the formula (VIIIa) in which $R_{34}$ and $R_{37}$ which can be identical or different are as defined above for $R_9$ and $R_{11}$; $R_{35}$ and $R_{36}$ which can be identical or different are $C_2$–$C_8$alkylene and $D_1$ is $C_2$–$C_8$alkylene, 2-hydroxytrimethylene, xylylene or a group of the formula (IXa) or (IXb) in which $R_{43}$ is a direct bond or $C_1$–$C_8$alkylene and $R_{44}$ is $C_4$–$C_8$alkylene, 3-oxapentane-1,5-diyl, cyclohexylenedimethylene or isopropylidenedicyclohexylene and, if w is 6, A is also a group of the formula (Xa) in which $R_{45}$ and $R_{49}$ which can be identical or different are as defined above for $R_9$ and $R_{11}$; $R_{46}$, $R_{47}$ and $R_{48}$ which can be identical or different are $C_2$–$C_8$alkylene and $D_2$ is as defined above for $D_1$.

Those compounds of the formula (I) are of special interest in which $R_2$ is $C_2$–$C_6$alkylene, $R_3$ is a group of the formula (II) or a group

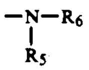

in which $R_5$ and $R_6$ which can be identical or different are $C_1$–$C_8$alkyl, cyclohexyl, benzyl, $C_2$–$C_3$alkyl which is substituted in the 2- or 3-position by methoxy, by ethoxy, by dimethylamino or diethylamino, allyl, tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl, and w is 2, 3 or 4, and, if w is 2, A is one of the groups of the formula (IVb)–(IVd) in which $R_9$ and $R_{11}$ which can be identical or different are hydrogen, $C_1$–$C_4$alkyl, cyclohexyl, 2,2,6,6-tetramethyl-4-piperidyl or 1,2,2,6,6-pentamethyl-4-piperidyl, $R_{10}$ is $C_2$–$C_6$alkylene, cyclohexylenedimethylene, methylenedicyclohexylene or $C_4$–$C_{12}$alkylene interrupted by 1 or 2 groups

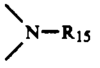

where $R_{15}$ is hydrogen, methyl or a group of the formula (Va) or (Vb) in which $R_{16}$ is $C_1$–$C_{17}$alkyl, cyclohexyl, phenyl or 2-(3,5-di-t-butyl-4-hydroxyphenyl)-ethyl and $R_{17}$ is $C_2$–$C_{18}$alkyl, cyclohexyl, t-butylcyclohexyl or 1,2,2,6,6-pentamethyl-4-piperidyl and m and n are zero, $R_{13}$ and $R_{14}$ which can be identical or different are as defined above for $R_9$ and $R_{11}$, p and q are 2 or 3 and r is zero or 1, and, if w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$–$C_6$-alkylene and $R_{20}$ is also $C_4$–$C_6$alkylene interrupted by a group

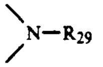

with $R_{29}$ being as defined above for $R_{15}$, and, if w is 4, A is a group of the formula (VII) in which $R_{30}$ and $R_{33}$ which can be identical or different are as defined above for $R_9$ and $R_{11}$; $R_{31}$ and $R_{32}$ which can be identical or different are $C_2$–$C_6$alkylene and x is 1, or A is a group of the formula (VIIIa) in which $R_{34}$ and $R_{37}$ which can be identical or different are as defined above for $R_9$ and $R_{11}$; $R_{35}$ and $R_{36}$ which can be identical or different are $C_2$–$C_6$alkylene and $D_1$ is a group of the formula (IXa) or (IXb) in which $R_{43}$ is $C_2$–$C_8$alkylene and $R_{44}$ is $C_4$–$C_6$alkylene, 3-oxapentane-1,5-diyl, cyclohexylenedimethylene or isopropylidenedicyclohexylene.

Those compounds of the formula (I) are of particular interest in which $R_1$ is hydrogen or methyl, $R_2$ is $-(CH_2)_{2-6}-$, $R_3$ is a group of the formula (II) with $R_1$ and $R_2$ being as defined above, w is 2, 3 or 4 and, if w is 2, A is one of the groups of the formula (IVb)–(IVd) in which $R_9$ and $R_{11}$ which can be identical or different are hydrogen, methyl, 2,2,6,6-tetramethyl-4-piperidyl or 1,2,2,6,6-pentamethyl-4-piperidyl, $R_{10}$ is $C_2$–$C_6$-alkylene, methylenedicyclohexylene, $C_4$–$C_{12}$alkylene interrupted by 1 or 2 groups

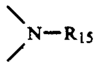

where $R_{15}$ is hydrogen, methyl or a group of the formula (Va) or (Vb) in which $R_{16}$ is $C_4$–$C_{17}$alkyl and $R_{17}$ is $C_2$–$C_{18}$alkyl or t-butylcyclohexyl, m and n are zero, $R_{13}$ and $R_{14}$ which can be identical or different are as defined above for $R_9$ and $R_{11}$, p and q are 2 or 3 and r is zero or 1, and, if w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$–$C_6$-alkylene and $R_{20}$ is also $C_4$–$C_6$alkylene interrupted by a group

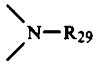

with $R_{29}$ being as defined above for $R_{15}$, and, if w is 4, A is a group of the formula (VII) in which $R_{30}$ and $R_{33}$ which can be identical or different are hydrogen or methyl, $R_{31}$ and $R_{32}$ which can be identical or different are $C_2$–$C_3$alkylene and x is 1.

A further preferred embodiment is that in which $R_1$ is hydrogen or methyl, $R_2$ is $C_2$–$C_6$alkylene, $R_3$ is a group of the formula (II) with $R_1$ and $R_2$ being as defined above and w is 2, 3 or 4, and, if w is 2, A is piperazine-1,4-diyl or a group of the formula (IVb) in which $R_9$ and $R_{11}$ which can be identical or different are hydrogen, methyl, 2,2,6,6-tetramethyl-4-piperidyl, or 1,2,2,6,6- pentamethyl-4-piperidyl, $R_{10}$ is $C_2$-$C_6$alkylene, methylenedicyclohexylene or $C_4$-$C_{12}$alkylene interrupted by 1 or 2 groups

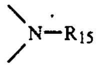

where $R_{15}$ is hydrogen, methyl or ($C_2$-$C_4$alkoxy)-carbonyl, and, if w is 3, A is a group of the formula (VIa) in which $R_{19}$ and $R_{22}$ which can be identical or different are hydrogen or methyl, $R_{20}$ is $C_2$-$C_6$alkylene or $C_4$-$C_6$alkylene interrupted by a

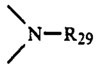

with $R_{29}$ being as defined above for $R_{15}$ and $R_{21}$ is $C_2$-$C_6$alkylene, and, if w is 4, A is a group of the formula (VII) where $R_{30}$ and $R_{33}$ which can be identical or different are hydrogen or methyl, $R_{31}$ and $R_{32}$ independently of one another are $C_2$-$C_3$alkylene and x is 1.

The compounds of the formula (I) can be prepared analogously to known processes, for example as described in U.S. Pat. No. 4,108,829.

It is preferable first to prepare the compounds of the formula (Ia)

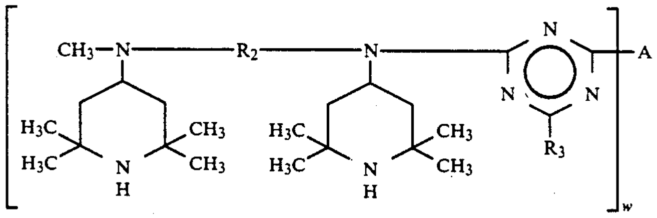

(Ia)

with $R_2$, $R_3$, A and w being as defined above, from which the corresponding compounds of the formula (I) with $R_1$ different from H can then be obtained.

The compounds of the formula (Ia) can be prepared, for example, by reacting, in any order, cyanuric chloride with the compounds of the formula (XIa)-(XIc)

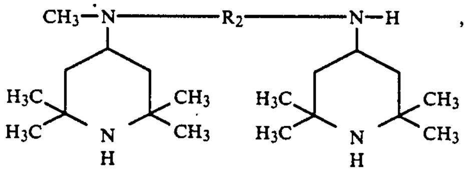

(XIa)

$R_3H$ , $A(H)_w$ (XIb) (XIc)

utilizing the appropriate molar ratios.

If $R_{10}$, $R_{20}$ and $R_{21}$ are $C_4$-$C_{12}$-alkylene interrupted by 1 or 2 groups

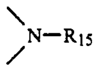

or by a groups

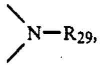

the compounds of the formula (Ia) are preferably prepared by reacting the corresponding compounds with $R_{15}$ and $R_{29}$=H with suitable alkylating or acylating reagents.

If A is a group of the formula (VIIIa) or (Xa), the compounds of the formula (Ia) are preferably prepared by reacting a compound of the formula (XIIa) or (XIIb) respectively

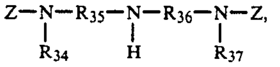

(XIIa)

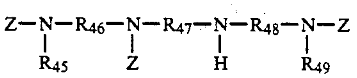

(XIIb)

in which Z is a group of the formula (XIII)

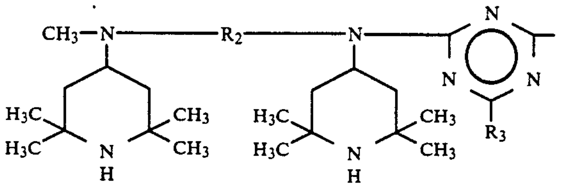

(XIII)

with the compound of the formula (XIV)

E-D-E (XIV)

in which E is, for example, chlorine or bromine and D is as defined above for $D_1$ or $D_2$, or with epichlorohydrin if $D_1$ and $D_2$ are 2-hydroxytrimethylene.

If $R_1$ is methyl, the compounds of the formula (I) are preferably prepared by reacting the corresponding compounds of the formula (Ia) with formaldehyde and formic acid (Eschweiler-Clarke reaction), or with formaldehyde and hydrogen in the presence of a hydrogenation catalyst, for example palladium or platinum.

In these reactions, the non-piperidine

amine groups and, under appropriate conditions, also the melamine

groups which may be present can also be methylated.

The reactions of cyanuric chloride with the compounds of the formula (XIa)-(XIc) are preferably carried out in an aromatic hydrocarbon solvent, for example toluene, xylene, trimethylbenzene or decalin, operating at a temperature from e.g. −30° to 40° C., preferably from −20° to 20° C., for the substitution of the first Cl, from e.g. 40° to 100° C., preferably from 50° to 90° C., for the substitution of the second Cl and from e.g. 100° to 200° C., preferably from 120° to 180° C., for the substitution of the third Cl.

The hydraulic acid liberated in the various reactions is neutralized with a preferably inorganic base, for example with sodium or potassium hydroxide or carbonate, in a quantity at least equivalent to the acid liberated.

The compounds of the formula (XIa) can be prepared, for example, according to scheme 1 by reacting a compound of the formula (XV) with 2 mols of 2,2,6,6-tetramethyl-4-piperidone to give an enamine-ketimine of the formula (XVI) which is then hydrogenated in the presence of a hydrogenation catalyst such as platinum, palladium or nickel.

SCHEME 1

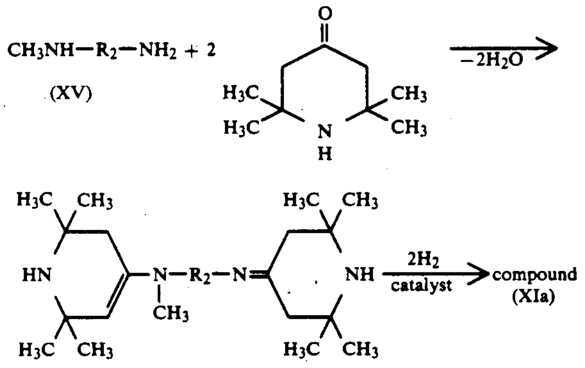

(XV) (XVI)

The reactions according to scheme 1 are preferably carried out in the same reactor without isolating the intermediate of the formula (XVI), operating without solvent or in the presence of an aliphatic or aromatic hydrocarbon solvent having a boiling point e.g. from 60° to 180° C. , preferably from 80° to 140° C.; the hydrogenation can also be carried out in the presence of a $C_1$-$C_4$alcohol.

The compounds of the formula (XIa) can also be prepared, for example, directly by catalytic hydrogenation of a mixture of 2,2,6,6-tetramethyl-4-piperidone and a compound of the formula (XV) in a molar ratio of 2/1, without solvent or in a $C_1$-$C_4$alcohol, preferably in the presence of an organic or inorganic acid, for example benzoic acid or sulphuric acid, in a quantity from 0.001 to 0.05 mol per mol of 2,2,6,6-tetramethyl-4-piperidone.

The other intermediates of the formula (XIb) and (XIc) are commercial products which can be prepared by known processes.

As mentioned at the outset, the compounds of the formula (I) are highly effective in improving the light stability, heat stability and oxidation stability of organic materials, in particular synthetic polymers and copolymers.

The invention therefore also relates to a composition comprising an organic material, which is susceptible to light-induced, thermal or oxidative degradation, and at least one compound of the formula (I).

Examples of organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3*a*. Hydrocarbon resins (for example $C_5$-$C_9$) and hydrogenated modifications thereof (for example tackyfiers).

4. Polystyrene, poly-(p-methylstyrene), poly-(α-methylstyrene).

5. Copolymers of styrene or -methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or o-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/ alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 9, 6/12 and 4/6, polyamide 11, polyamide 12, aromatic polyamides obtained by condensation of m-xylylenediamine and adipic acid; polyamides prepared from hexamethylenediamine and isophthalic or/and terephthalic acid and optionally an elastomer as modifier, for example poly-2,4,4-trimethylhexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoates as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crossslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latices or latices of carboxylated styrene/butadiene copolymers.

The compounds of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I) relative to the weight of the material to be stabilized, preferably from 0.05 to 1%.

The compounds of the formula (I) can be incorporated in the polymeric materials by various processes, such as e.g. dry mixing in the form of powder, or wet mixing in the form of solutions or suspensions or also in the form of a masterbatch; in such operations, the polymer can be used in the form of e.g. powder, granules, solutions, suspensions or in the form of latices.

The materials stabilized with the products of the formula (I) can be used for the production of e.g. mouldings, filmed, tapes, monofilaments, surface coatings and the like.

If desired, other conventional additives for synthetic polymers, such as e.g. antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tertbutyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis-(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)- 4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate, bis(3-tert-butyl-4-hydroxy-5-methylphenyl)dicyclopentadiene, bis[2-(3'-tert-butyl-2'-hydroxy-5'-methylbenzyl)-6-tert-butyl-4 methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-secbutyl-5'-tert-butyl, 4'-octoxy,3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyanoβ-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentmethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis-(3,3,5,5-tetramethyl-piperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tertbutyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o-and p-ethoxy-disubstituted oxanilides.

2.8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxy- phenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3.5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylene-diphosphonite, 3,9-bis(2,4-di-tert-butylphenoxy)-2,4,8,10-tetra-oxa-3,9-diphosphaspiro[5.5]-undecane.

5. Peroxide scavengers, for example esters of $\beta$-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis($\beta$-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

In order to illustrate the present invention more clearly, several examples of the preparation of compounds of the formula (I) are described below; these examples are given by way of illustration only and do not imply any restriction. The compounds of Examples 2, 8, 10, 14 and 17 are especially preferred compounds of formula (I).

EXAMPLE 1: Preparation of the Compound

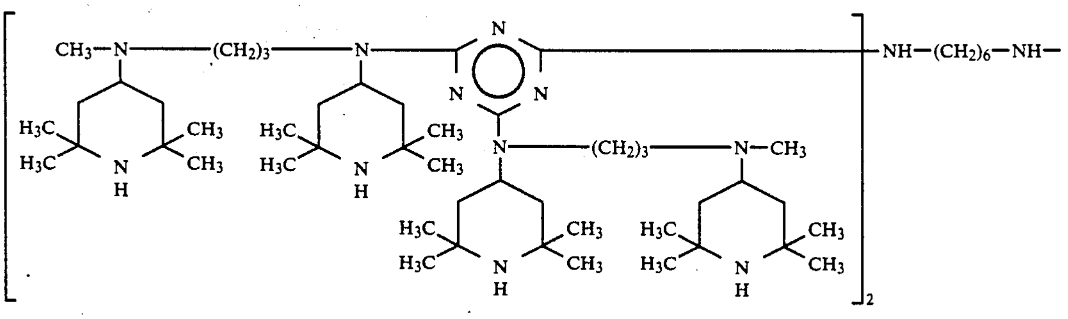

A solution of 24.1 g (0.13 mol) of cyanuric chloride in 150 ml of mesitylene is slowly added to a solution, cooled to −20° C., of 95.2 g (0.26 mol) of N-methyl-N,N'-bis-(2,2,6,6-tetramethyl-4-piperidyl)-1,3-propanediamine in 120 ml of mesitylene, while maintaining the temperature at −15° to −20° C.

The mixture is stirred for one hour at ambient temperature, a solution of 10.4 g (0.26 mol) of sodium hydroxide in 30 ml of water is added and the mixture is heated for 4 hours at 60° C. The aqueous phase is separated off, 7.6 g (0.065 mol) of 1,6-hexanediamine and 35.9 g (0.26 mol) of ground anhydrous potassium carbonate are added and the mixture is heated for 18 hours under reflux with elimination of the water of reaction.

After cooling to about 50° C., the reaction mixture is filtered and evaporated in vacuo (2 mbar). The resulting oily residue is taken up in aqueous acetone (10% of water), from which the product of melting point 70°-74° C. crystallizes.

Analysis for $C_{100}H_{194}N_{24}$

Calculated: C=69.32%; H=11.28%; N=19.40%

Found: C=69.01%; H=11.20%; N=19.25%.

EXAMPLES 2-11

Following the procedure described in Example 1, but using the appropriate reagents, the following compounds of the formula

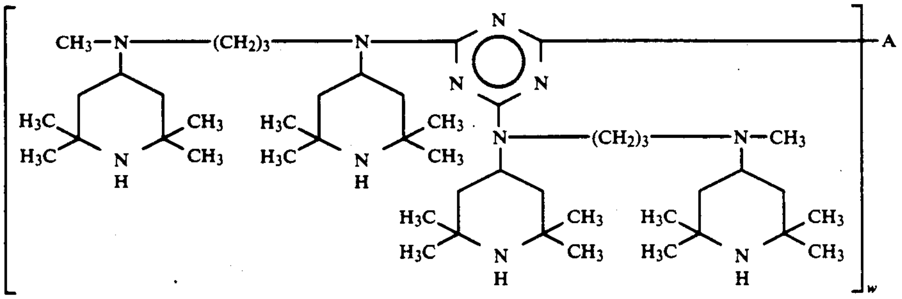

are prepared.

| Example | W | A | m.p. (°C.) |
|---|---|---|---|
| 2 | 2 | 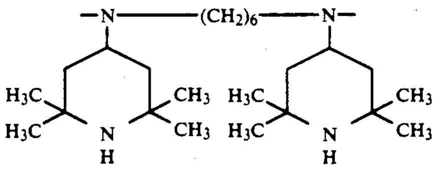 | 91-94 |
| 3 | 2 | 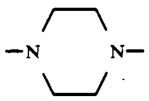 | 233-236 |
| 4 | 2 | 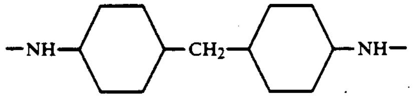 | 82-87 |
| 5 | 2 | $-NH-(CH_2)_3-NH-(CH_2)_3-NH-$ | 53-57 |
| 6 | 3 | $-NH-(CH_2)_2-N(-)-(CH_2)_2-NH-$ | 90-94 |
| 7 | 3 | $-NH-(CH_2)_3-N(-)-(CH_2)_3-NH-$ | 100-105 |
| 8 | 3 | $-NH-(CH_2)_6-N(-)-(CH_2)_6-NH-$ | 79-83 |
| 9 | 3 | $-NH-(CH_2)_3-N(-)-(CH_2)_2-NH-(CH_2)_3-NH-$ | 96-100 |
| 10 | 3 | $-NH-(CH_2)_3-N(-)-(CH_2)_2-N(COOC_4H_9)-(CH_2)_3-NH-$ | 72-76 |
| 11 | 4 | $-NH-(CH_2)_3-N(-)-(CH_2)_2-N(-)-(CH_2)_3-NH-$ | 109-113 |

EXAMPLE 12: Preparation of the Compound

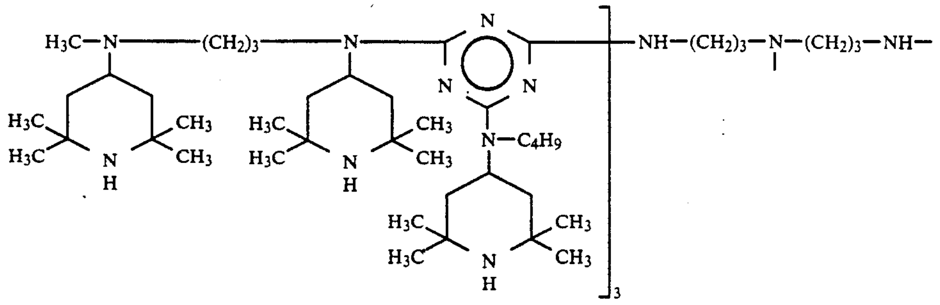

11.5 g (0.054 mol) of N-(2,2,6,6-tetramethyl-4-piperidyl)-n-butylamine are added to a solution, cooled to −20° C., of 10.0 g (0.054 mol) of cyanuric chloride in 100 ml of xylene, while maintaining the temperature at −15° C. to −20° C. The mixture is stirred one hour at 0° C., a solution of 2.27 g (0.057 mol) of sodium hydroxide in 10 ml of water is added and the mixture is stirred for 2 hours at room temperature. 19.84 g (0.054 mol) of N-methyl-N,N'-bis-(2,2,6,6-tetramethyl-4-piperidyl)-1,3-propanediamine are added and the mixture is heated one hour at 40° C. A solution of 2.27 g (0.057 mol) of sodium hydroxide is added at 35° C. and the mixture is heated three hours at 60° C. After cooling to room temperature, the aqueous phase is separated off, 2.36 g (0.018 mol) of bis-(3-aminopropyl)amine and 4.32 g (0.108 mol) of sodium hydroxide are added and the mixture is heated for 10 hours under reflux with elimination of the water of reaction. After cooling, the mixture is washed repeatedly with water and the solution evaporated in vacuo (2 mbar). The product has a melting point of 87°-92° C.

Analysis for $C_{120}H_{230}N_{30}$

Calculated: C=68.85% ; H=11.07% ; N=20.07%

Found : C=68.67% ; H=10.95% ; N=19.90%.

EXAMPLE 13: Preparation of the Compound

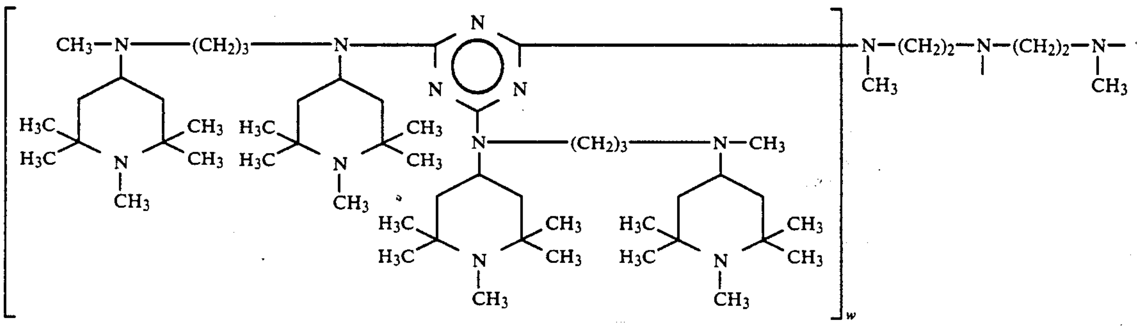

10.1 g (0.004 mol) of the compound from Example 6 are dissolved in a solution of 9.3 g (0.202 mol) of formic acid in 70 ml of water.

6.72 g (0.224 mol) of paraformaldehyde are added and the mixture is heated under reflux for 10 hours.

After cooling to ambient temperature, a solution of 16 g (0.4 mol) of sodium hydroxide in 50 ml of water is added; the resulting precipitate is separated off by filtration, washed repeatedly with water and dried at 100° C. in vacuo (2 mbar). The product has a melting point of 114°-118° C.

Analysis for $C_{159}H_{308}N_{36}$

Calculated: C=70.10%; H=11.39%; N=18.51%

Found: C=69.90%, H=11.34%; 18.52%.

Examples 14-16

Following the procedure described in Example 13, but using the appropriate reagents, the following compounds of the formula

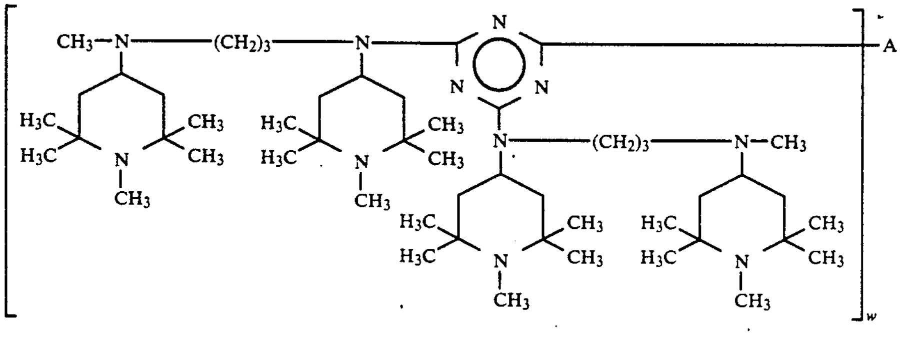

are prepared.

| Example | W | A | m.p. (°C.) |
|---|---|---|---|
| 14 | 3 | 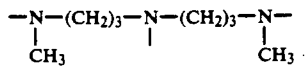 | 97-101 |
| 15 | 3 | 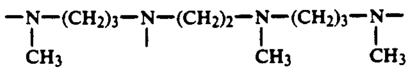 | 105-109 |
| 16 | 4 | 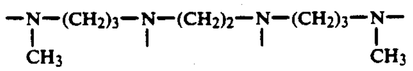 | 116-121 |

EXAMPLE 17: Preparation of the Compound

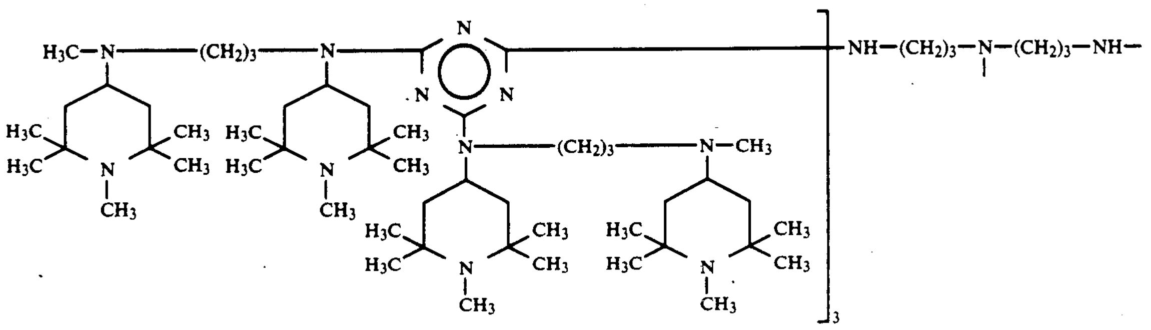

A mixture consisting of 3.4 g (0.074 mol) of formic acid and of a solution obtained by dissolving 2.56 g (0.083 mol) of paraformaldehyde in 4.6 ml of 2% aqueous NaOH solution is added in the course of about 2 hours to a solution of 14.05 g (0.005 mol) of the product described in example 7 in 30 ml of xylene, heated to 110° C., the water added and the water of reaction simultaneously being separated off azeotropically.

The mixture is then cooled to 70°-80° C. and a solution of 0.8 g of sodium hydroxide in 10 ml of water is added. The aqueous layer is separated off and the mixture is dehydrated, separating off the water azeotropically. The solution is then evaporated in vacuo giving a product of melting point 95°-99° C.

Analysis for $C_{159}H_{308}N_{36}$

Calculated: C=70.10% ; H=11.40% ; N=18.51%

Found: C=69.62% ; H=11.25% ; N=18.32%.

EXAMPLE 18: Light-stabilizing Action in Polypropylene Tapes 1 g of each of the compounds indicated in Table 1, 0.5 g of tris-(2,4-di-t-butylphenyl) phosphite, 0.5 g of pentaerythritol tetrakis[3-(3,5-di-t-butyl-4-hydroxyphenyl)-propionate] and 1 g of calcium stearate are mixed in a slow mixer with 1,000 g of polypropylene powder of melt index=2 g/10 minutes (measured at 230° C. and 2.16 kg).

The mixtures are extruded at 200°-220° C. to give polymer granules which are then converted into stretched tapes of 50 pm thickness and 2.5 mm width, using a pilot-type apparatus (Leonard-Sumirago (VA) Italy) and operating under the following conditions:

extruder temperature: 210°-230° C.
head temperature: 240°-260° C.
stretch ratio: 1:6

The tapes thus prepared are exposed, mounted on a white card, in a 65 WR Weather-O-Meter (ASTM G26-77) at a black panel temperature of 63° C.

The residual tenacity is measured on samples, taken after various times of exposure to light, by means of a constant-speed tensometer; the exposure time (in hours) needed to halve the initial tenacity is then calculated ($T_{50}$).

Tapes prepared under the same conditions as indicated above, but without the addition of stabilizer, are exposed for comparison.

The results obtained are shown in Table 1:

TABLE 1

| Stabilizer | $T_{50}$ (hours) |
|---|---|
| without stabilizer | 500 |
| compound from Example 1 | 3,050 |
| compound from Example 2 | 3,140 |
| compound from Example 4 | 3,190 |
| compound from Example 6 | 2,520 |
| compound from Example 7 | 2,150 |
| compound from Example 8 | 3,270 |
| compound from Example 9 | 2,600 |
| compound from Example 11 | 2,520 |
| compound from Example 13 | 3,090 |

EXAMPLE 19: Light-stabilizing Action in Polypropylene Fibres 2.5 g each of the products indicated in Table 2, 0.5 g of tris-(2,4-di-t-butylphenyl phosphite, 0.5 g of calcium monoethyl 3,5-di-t-butyl-4-hydroxybenzylphosphonate, 1 g of calcium stearate and 2.5 g of titaniumdioxide are mixed in a slow mixer with 1,000 g of polypropylene powder of melt index=12 g/10 minutes (measured at 230° C. and 2.16 kg).

The mixtures are extruded at 200°-220° C. to give polymer granules which are then converted into fibres, using a pilot-type apparatus (Leonard-Sumirago (VA) Italy) and operating under the following conditions:

extruder temperature: 200°-230° C.

head temperature: 255°-260° C.
stretch ratio: 1:3.5
denier: 11 dtex per filament The fibres thus prepared are exposed, mounted on a white card, in a model 65 WR Weather-O-Meter (ASTM G 26-77) at a black panel temperature of 63° C.

The residual tenacity is measured on samples, taken after various times of exposure to light, by means of a constant-speed tensometer; the exposure time in hours) needed to halve the initial tenacity is then calculated ($T_{50}$).

Fibres prepared under the same conditions as indicated above, but without the addition of compounds according to the invention, are exposed for comparison.

The results obtained are shown in Table 2:

TABLE 2

| Stabilizer | $T_{50}$ (hours) |
|---|---|
| without stabilizer | 150 |
| compound from Example 1 | 1,640 |
| compound from Example 2 | 1,830 |
| compound from Example 3 | 1,650 |
| compound from Example 5 | 1,640 |
| compound from Example 6 | 1,510 |
| compound from Example 7 | 1,690 |
| compound from Example 8 | 1,840 |
| compound from Example 9 | 1,510 |
| compound from Example 10 | 1,780 |
| compound from Example 11 | 1,470 |
| compound from Example 12 | 1,660 |
| compound from Example 13 | 1,500 |
| compound from Example 14 | 1,840 |
| compound from Example 15 | 1,520 |
| compound from Example 17 | 1,730 |

What is claimed is:

1. A compound of formula I (I)

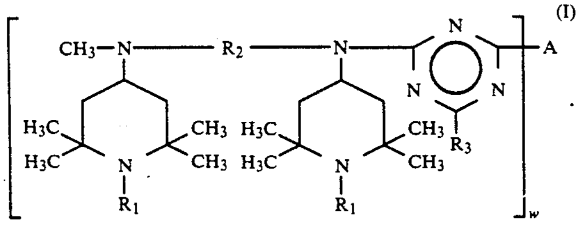

in which $R_1$ is hydrogen, $C_1$-$C_8$alkyl, O°, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono, di-or tri-substituted on the phenyl by $C_1$-$C_4$alkyl, $C_1$-$C_8$-acyl or $C_2$-$C_4$alkyl substituted in the 2-, 3- or 4-position by OH;

$R_2$ is $C_2$-$C_{12}$alkylene;

$R_3$ is a group of formula II (II)

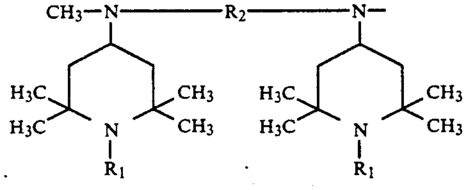

with $R_1$ and $R_2$ being as defined above, or $R_3$ is a group $-OR_4$, $-SR_4$ or

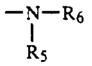

in which $R_4$ is $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl, phenyl which is unsubstituted or mono, di- or tri-substituted by $C_1$-$C_4$alkyl, $C_7$-$C_9$-phenylalkyl which is unsubstituted or mono, di- or tri-substituted on the phenyl by $C_1$-$C_4$alkyl, or a group of the formula (III)

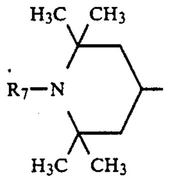

(III)

where $R_7$ has any of the meanings given for $R_1$;

$R_5$ and $R_6$ which can be identical or different are hydrogen, $C_1$-$C_{18}$alkyl, $C_5$-$C_{12}$cycloalkyl which is unsubstituted or mono, di- or tri-substituted by $C_1$-$C_4$alkyl, $C_7$-$C_9$-phenylalkyl which is unsubstituted or mono-, di- or tri-substituted on the phenyl by $C_1$-$C_4$alkyl, $C_2$-$C_4$alkyl substituted in the 2-, 3- or 4-position by OH, by $C_1$-$C_8$alkoxy or by di-($C_1$-$C_4$alkyl)-amino, $C_3$-$C_{18}$-alkenyl, tetrahydrofurfuryl or a group of the formula (III), or $R_5$ and $R_6$, together with the nitrogen atom to which they are linked, form part of a 5-membered to 7-membered heterocyclic ring which is 1 -pyrrolidyl, 1-piperidyl, 4-morpholinyl, 4-methyl-1-piperazinyl, 1-hexahydroazepinyl, 5,5,7-trimethyl-1-homopiperazinyl or 4,5,5,7-tetramethyl-1-homopiperazinyl; and w is an integer from 2 to 6; and when w is 2, A is one of the groups of the formula (IVa)-(IVd)

$-O-R_8-O-$, (IVa)

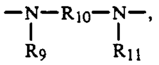

(IVb)

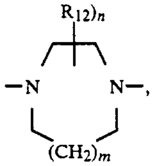

(IVc)

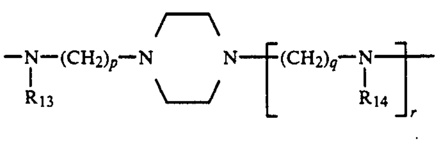

(IVd)

in which $R_8$ is $C_2$-$C_{12}$alkylene, cyclohexylene, cyclohexylenedimethylene, methylenedicyclohexylene, ($C_2$-$C_6$alkylidene)-dicyclohexylene, phenylene, ($C_2$-$C_6$alkylidene)-diphenylene, xylylene or $C_4$-$C_{12}$alkylene interrupted by 1, 2 or 3 oxygen atoms; $R_9$ and $R_{11}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$–$C_4$-alkyl, or a group of the formula (III); $R_{10}$ is as defined above for $R_8$ or $C_4$–$C_{12}$alkylene interrupted by 1 or 2 groups

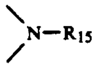

where $R_{15}$ has any of the meanings given above for $R_9$ and $R_{11}$, or is one of the groups of the formula (Va)-Vd)

$-COR_{16}$, $-COOR_{17}$, $-COCOOR_{17}$, $-SO_2R_{18}$ (Va) (Vb) (Vc) (Vd)

where $R_{16}$ is hydrogen, $C_1$–$C_{18}$alkyl, $C_5$–$C_{12}$cycloalkyl which is unsubstituted or mono, di- or tri-substituted by $C_1$–$C_4$alkyl, $C_2$–$C_{18}$alkenyl, phenyl which is unsubstituted or mono-, di- or tri-substituted by $C_1$–$C_4$-alkyl or an OH group or mixture thereof, $C_7$–$C_9$phenylalkyl which is unsubstituted or mono-, di-or tri-substituted on the phenyl by $C_1$–$C_4$alkyl or an OH group or mixture thereof;

$R_{17}$ is $C_1$–$C_{18}$alkyl, $C_5$–$C_{12}$cycloalkyl which is unsubstituted or mono-, di- or tri-substitutedc by $C_1$–$C_4$alkyl, $C_3$–$C_{18}$alkenyl or a group of the formula (III); $R_{18}$ is $C_1$–$C_{18}$alkyl or phenyl which is unsubstituted or mono-, di- or tri-substituted by $C_1$–$C_4$alkyl; m is zero or 1; $R_{12}$ is hydrogen or methyl; n is zero, 1, 2, 3 or 4; $R_{13}$ and $R_{14}$ which are identical or different are as defined above for $R_9$ and $R_{11}$; p and q which can be identical or different are integers from 2 to 6; and r is zero or 1;

when w is 3, A is one of the groups of the formula (VIa)-(VIc)

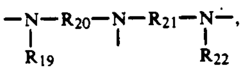

(VIa)

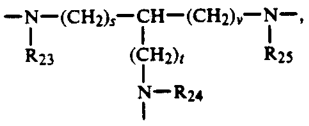

(VIb)

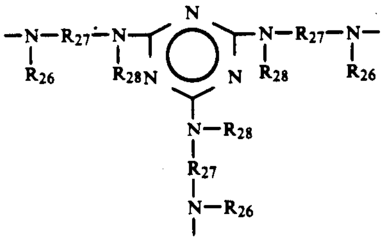

(VIc)

in which $R_{19}$, $R_{22}$, $R_{23}$, $R_{24}$, $R_{25}$, $R_{26}$ and $R_{28}$ which can be identical or different are as defined above for $R_9$ and $R_{11}$; $R_{20}$ and $R_{21}$ which can be identical or different are $C_2$–$C_{12}$alkylene or $C_4$–$C_{12}$alkylene interrupted by a group

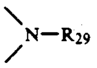

with $R_{29}$ being defined as above for $R_{15}$; s and v which can be identical or different are integers from 2 to 6; t is zero or 1;

and $R_{27}$ is $C_2$–$C_{12}$alkylene, and when w is 4,5 or 6, A is additionally a group of the formula (VII)

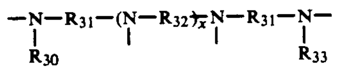

(VII)

in which $R_{30}$ and $R_{33}$ which can be identical or different are as defined above for $R_9$ and $R_{11}$; $R_{31}$ and $R_{32}$ which can be identical or different are $C_2$–$C_{12}$alkylene; and xi is 1, 2 or 3, and, when w is 4, A is also one of the groups of the formula (VIIIa)-(VIIIc)

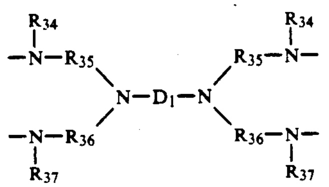

(VIIIa)

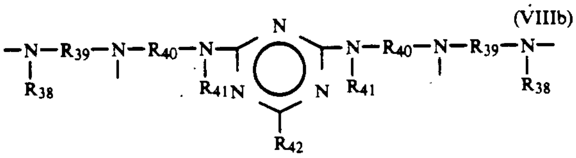

(VIIIb)

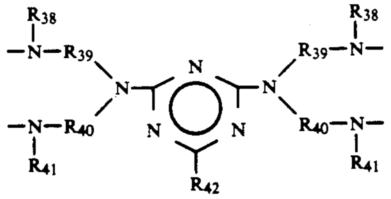

(VIIIc)

in which $R_{34}$, $R_{37}$, $R_{38}$ and $R_{41}$ which can be identical or different are as defined above for $R_9$ and $R_{11}$; $R_{35}$, $R_{36}$, $R_{39}$ and $R_{40}$ which can be identical or different are $C_2$–$C_{12}$alkylene; $D_1$ is $C_2$–$C_{12}$alkylene, 2-hydroxytrimethylene, $-CH_2CO-$, xylylene or one of the groups of the formula (IXa) or (IXb)

$-COR_{43}CO-$ $-COOR_{44}OOC-$ (IXa) (IXb)

in which $R_{43}$ is a direct bond, $C_1$–$C_{12}$alkylene, cyclohexylene or phenylene; $R_{44}$ is as defined above for $R_8$; and $R_{42}$ is as defined above for $R_3$; and when w is 6, A is also one of the groups of the formula (Xa)-(Xc)

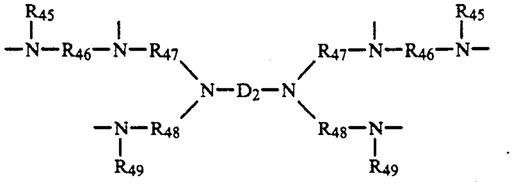

(Xa)

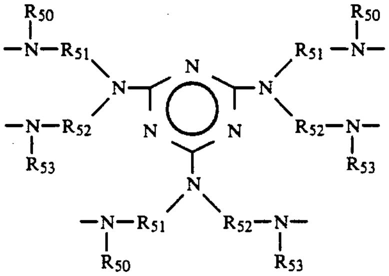

(Xb)

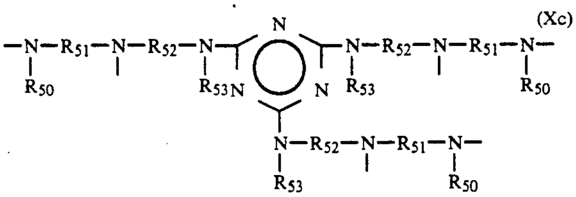

(Xc)

in which $R_{45}$, $R_{49}$, $R_{50}$ and $R_{53}$ which can be identical or different are as defined above for $R_9$ and $R_{11}$; $R_{46}$, $R_{47}$, $R_{48}$, $R_{51}$ and $R_{52}$ which can be identical or different are $C_2$–$C_{12}$alkylene; and $D_2$ is as defined above for $D_1$.

2. A compound of the formula (I) according to claim 1, wherein $R_1$ is hydrogen, $C_1$–$C_4$alkyl, OH, $C_6$–$C_{12}$alkoxy, $C_5$–$C_8$cycloalkoxy, allyl, benzyl, acetyl or 2-hydroxyethyl.

3. A compound of the formula (I) according to claim 1, wherein $R_2$ is $C_2$–$C_{10}$alkylene, $R_3$, is a group of the formula (II), a group —$OR_4$, —$SR_4$ or

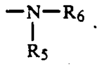

in which $R_4$ is $C_1$–$C_{12}$alkyl, $C_5$–$C_8$cycloalkyl which is unsubstituted or mono-, di- or tri-substituted by $C_1$–$C_4$alkyl, $C_3$–$C_{12}$alkenyl, phenyl, benzyl or a group of the formula (III), $R_5$ and $R_6$ which can be identical or different are hydrogen, $C_1$–$C_{18}$alkyl, $C_5$–$C_8$cycloalkyl which is unsubstituted or mono-, di- or tri-substituted by $C_1$–$C_4$alkyl, benzyl, $C_2$–$C_3$alkyl substituted in the 2- or 3-position by OH, by $C_1$–$C_4$alkoxy or by di-($C_1$–$C_4$alkyl)-amino, allyl, oleyl, tetrahydrofurfuryl or a group of the formula (III), or the group

is 1-pyrrolidyl, 1-piperidyl, 4-morpholinyl or 1-hexahydroazepinyl, 1 is an integer from 2 to 6 and, if 1 is 2, A is one of the groups of formula (IVa)–(IVd) in which $R_8$ is $C_2$–$C_{10}$ alkylene, cyclohexylene, cyclohexylenedimethylene, methylenedicyclohexylene, isopropylidenedicyclohexylene, isopropylidenediphenylene or $C_4$–$C_{10}$alkylene interrupted by 1, 2 or 3 oxygen atoms, $R_9$ and $R_{11}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, benzyl or a group of the formula (III), $R_{10}$ is as defined above for $R_8$ or is $C_4$–$C_{12}$alkylene interrupted by 1 or 2 group

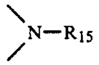

where $R_{15}$ has any of the meanings given for $R_9$ and $R_{11}$, or is one of the groups of the formula (Va)–(Vd) in which $R_{16}$ is hydrogen, $C_1$–$C_{17}$alkyl, $C_5$–$C_8$cycloalkyl which is unsubstituted or mono-, di-or tri-substituted by $C_1$–$C_4$alkyl, $C_2$–$C_{17}$alkenyl, phenyl which is unsubstituted or mono-, di- or tri-substituted by $C_1$–$C_4$alkyl and/or an OH group, $C_7$–$C_8$phenylalkyl which is unsubstituted or mono-, di- or trisubstituted on the phenyl by $C_1$–$C_4$alkyl and/or an OH group, $R_{17}$ is $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (III) and $R_{18}$ is $C_1$–$C_{12}$alkyl, phenyl or tolyl, m is zero or 1, $R_{12}$ is hydrogen or methyl, n is zero, 1, 2, 3 or 4, $R_{13}$ and $R_{14}$ which can be identical or different are as defined above for $R_9$ and $R_{11}$, p and q which can be identical or different are 2 or 3 and r is zero or 1, and, if 1 is 3, A is one of the groups of the formula (VIa)–(VIc) in which $R_{19}$, $R_{22}$, $R_{23}$, $R_{24}$, $R_{25}$, $R_{26}$ and $R_{28}$ which can be identical or different are as defined above for $R_9$ and $R_{11}$; $R_{20}$ and $R_{21}$ which can be identical or different are $C_2$–$C_{10}$alkylene or $C_4$–$C_{12}$alkylene which is interrupted by a group

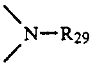

with $R_{29}$ being as defined above for $R_{15}$, s and v which can be i or different are integers from 2 to 6, t is zero or 1 and $R_{27}$ is $C_2$–$C_{10}$alkylene, and, when w is 4, 5 or 6, A is a group of the formula (VII) in which $R_{30}$ and $R_{33}$ which can be identical or different are as defined above for $R_9$ and $R_{11}$; $R_{31}$ and $R_{32}$ which can be identical or different are $C_2$–$C_{10}$alkylene; and x is 1, 2 or 3, and, when w is 4, A can also be one of the groups of the formula (VIIIa)–(VIIIc) in which $R_{34}$, $R_{37}$, $R_{38}$ and $R_{41}$ which can be identical or different are as defined above for $R_9$ and $R_{11}$; $R_{35}$, $R_{36}$, $R_{39}$ and $R_{40}$ which can be identical or different are $C_2$–$C_{10}$alkylene, $D_1$ is $C_2$–$C_{10}$alkylene, 2-hydroxytrimethylene, —$CH_2CO$—, xylylene or one of the groups of the formula (IXa) or (IXb) in which $R_{43}$ is a direct bond or $C_1$–$C_{10}$alkylene, $R_{44}$ is as defined above for $R_8$; and $R_{42}$ is as defined above for $R_3$ and, when w is 6, A is also one of the groups of the formula (Xa)–(Xc) in which $R_{45}$, $R_{49}$, $R_{50}$ and $R_{53}$ which can be identical or different are as defined above for $R_9$ and $R_{11}$; $R_{46}$, $R_{47}$, $R_{48}$, $R_{51}$ and $R_{52}$ which can be identical or different are $C_2$–$C_{10}$alkylene; and $D_2$ is as defined above for $D_1$.

4. A compound of the formula (I) according to claim 1, wherein $R_2$ is $C_2$–$C_8$alkylene; $R_3$ is a group of the formula (II), a group —$OR_4$ or

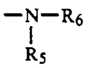

in which $R_4$ is $C_1$–$C_8$alkyl, cyclohexyl which is unsubstituted or mono-, di- or tri-substituted by $C_1$–$C_4$alkyl, allyl, undecenyl, phenyl, benzyl or a group of the formula (III); $R_5$ and $R_6$ which can be identical or different are hydrogen, $C_1$–$C_{12}$alkyl, cyclohexyl which is unsubstituted or mono-, di- or tri-substituted by $C_1$–$C_4$alkyl, benzyl, $C_2$–$C_3$alkyl substituted in the 2- or 3-position by OH, by methoxy, by ethoxy, by dimethylamino or by diethylamino, allyl, tetrahydrofurfuryl or a group of the formula (III), or the group

is 4-morpholinyl; w is an integer from 2 to 6; and, when w is 2, A is one of the groups of the formula (IVb-)-(IVd) in which $R_9$ and $R_{11}$ which can be identical or different are hydrogen, $C_1$–$C_8$alkyl, cyclohexyl which is unsubstituted or mono-, di- or trisubstituted by $C_1$–$C_4$alkyl, benzyl or a group of the formula (III); $R_{10}$ is $C_2$–$C_8$alkylene, cyclohexylenedimethylene, methylenedicyclohexylene, $C_4$–$C_8$alkylene interrupted by 1 or 2 oxygen atoms or $C_4$–$C_{12}$alkylene interrupted by 1 or 2 groups

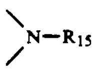

where $R_{15}$ has any of the meanings given for $R_9$ and $R_{11}$, or is one of the groups of the formula (Va)-(Vc) in which $R_{16}$ is $C_1$–$C_{17}$alkyl, cyclohexyl which is unsubstituted or mono-, di- or tri-substituted by $C_1$–$C_4$alkyl, $C_2$–$C_{10}$alkenyl, phenyl, 3,5-di-t-butyl-4-hydroxyphenyl, benzyl or 2-(3,5-di-t-butyl-4-hydroxyphenyl)ethyl; $R_{17}$ is $C_1$–$C_{18}$alkyl, cyclohexyl which is unsubstituted or mono-, di- or tri-substituted by $C_1$–$C_4$alkyl, allyl, undecenyl, oleyl or a group of the formula (III); m is zero or 1; $R_{12}$ is hydrogen or methyl; n is zero, 1, 2 or 3; $R_{13}$ and $R_{14}$ which can be identical or different are as defined above for $R_9$ and $R_{11}$; p and q which can be identical or different are 2 or 3; and r is zero or 1;, and, when w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$–$C_8$alkylene and $R_{20}$ is also $C_4$–$C_{12}$alkylene interrupted by a group

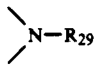

with $R_{29}$ being as defined above for $R_{15}$; and, when w is 4, 5 or 6, A is a group of the formula (VII) in which $R_{30}$ and $R_{33}$ which can be identical or different are as defined above for $R_9$ and $R_{11}$; $R_{31}$ and $R_{32}$ which can be identical or different are $C_2$–$C_8$alkylene and x is 1, 2 or 3; and, when w is 4, A is also a group of the formula (VIIIa) in which $R_{34}$ and $R_{37}$ which can be identical or different are as defined above for $R_9$ and $R_{11}$; $R_{35}$ and $R_{36}$ which can be identical or different are $C_2$–$C_8$alkylene and $D_1$ is $C_2$–$C_8$alkylene, 2-hydroxytrimethylene, xylylene or a group of the formula (IXa) or (IXb) in which $R_{43}$ is a direct bond or $C_1$–$C_8$alkylene; and $R_{44}$ is $C_4$–$C_8$alkylene, 3-oxapentane-1,5-diyl, cyclohexylenedimethylene or isopropylidenedicyclohexylene; and, when w is 6, A is also a group of the formula (Xa) in which $R_{45}$ and $R_{49}$ which can be identical or different are as defined above for $R_9$ and $R_{11}$; $R_{46}$, $R_{47}$ and $R_{48}$ which can be identical or different are $C_2$–$C_8$alkylene and $D_2$ is as defined above for $D_1$.

5. A compound of the formula (I) according to claim 1, wherein $R_2$ is $C_2$–$C_6$alkylene; $R_3$ is a group of the formula (II) or a group

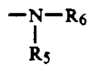

in which $R_5$ and $R_6$ which can be identical or different are $C_1$–$C_8$alkyl, cyclohexyl, benzyl, $C_2$–$C_3$ which is substituted in the 2- or 3-position by methoxy, by ethoxy, by dimethylamino or diethylamino, allyl tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl; and w is 2, 3 or 4, and, when w is 2, A is one of the groups of the formula (IVb)-(IVd) in which $R_9$ and $R_{11}$ which can be identical or different are hydrogen, $C_1$–$C_4$alkyl, cyclohexyl, 2,2,6,6-tetramethyl-4-piperidyl or 1,2,2,6,6-pentamethyl-4-piperidyl; $R_{10}$ is $C_2$–$C_6$alkylene, cyclohexylenedimethylene, methylenedicyclohexylene or $C_4$–$C_{12}$alkylene interrupted by 1 or 2 groups

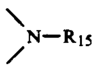

where $R_{15}$ is hydrogen, methyl or a group of the formula (Va) or (Vb) in which $R_{16}$ is $C_1$–$C_{17}$alkyl, cyclohexyl, phenyl or 2-(3,5-di-t-butyl-4-hydroxyphenyl)ethyl; and $R_{17}$ is $C_2$–$C_{18}$alkyl, cyclohexyl, t-butylcyclohexyl or 1,2,2,6,6-pentamethyl-4-piperidyl; and m and n are zero; $R_{13}$ and $R_{14}$ which can be identical or different are as defined above for $R_9$ and $R_{11}$, p and q are 2 or 3 and r is zero or 1, and, when w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$–$C_6$-alkylene and $R_{20}$ is also $C_4$–$C_6$alkylene interrupted by a group N-$R_{29}$ with $R_{29}$ being as defined above for $R_{15}$; and, when w is 4, A is a group of the formla (VII) in which $R_{30}$ and $R_{33}$ which can be identical or different are as defined above for $R_9$ and $R_{11}$; $R_{31}$ and $R_{32}$ which can be identical or different are $C_2$–$C_6$alkylene; and x is 1, or A is a group of the formula (VIIIa) in which $R_{34}$ and $R_{37}$ which can be identical or different are as defined above for $R_9$ and $R_{11}$; $R_{35}$ and $R_{36}$ which can be identical or different are $C_2$–$C_6$alkylene; and $D_1$ is a group of the formula (IXa) or (IXb) in which $R_{43}$ is $C_2$–$C_8$alkylene; and $R_{44}$ is $C_4$–$C_6$alkylene, 3-oxa-pentane-1,5-diyl, cyclohexylenedimethylene or isopropylidenedicyclohexylene.

6. A compound of the formula (I) according to claim 1, wherein $R_1$ is hydrogen or methyl; $R_2$ is $-(CH_2)_{2-6}-$; $R_3$ is a group of the formula (II) with $R_1$ and $R_2$ being as defined above; w is 2, 3 or 4 and, when w is 2, A is one of the groups of the formula (IVb)-(IVd) in which $R_9$ and $R_{11}$ which can be identical or different are hydrogen, methyl, 2,2,6,6-tetramethyl-4-piperidyl or 1,2,2,6,6-pentamethyl-4-piperidyl; $R_{10}$ is $C_2$-$C_6$-alkylene, methylenedicyclohexylene, $C_4$-$C_{12}$alkylene interrupted by 1 or 2 group

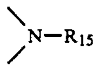

where $R_{15}$ is hydrogen, methyl or a group of the formula (Va) or (Vb) in which $R_{16}$ is $C_4$-$C_{17}$alkyl and $R_{17}$ is $C_2$-$C_{18}$alkyl or t-butylcyclohexyl; m and n are zero; $R_{13}$ and $R_{14}$ which can be identical or different are as defined above for $R_9$ and $R_{11}$; p and q are 2 or 3; and r is zero or 1; and, when w is 3, A is a group of the formula (VIa) in which $R_{19}$ and $R_{22}$ which can be identical or different are as defined above for $R_9$ and $R_{11}$; $R_{20}$ and $R_{21}$ which can be identical or different are $C_2$-$C_6$-alkylene and $R_{20}$ is also $C_4$-$C_6$alkylene interrupted by a group

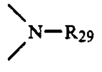

with $R_{29}$ being as defined above for $R_{15}$; and, when w is 4, A is a group of the formula (VII) in which $R_{30}$ and $R_{33}$ which can be identical or different are hydrogen or methyl; $R_{31}$ and $R_{32}$ which can be identical or different are $C_2$-$C_3$alkylene and x is 1.

7. A compound of the formula (I) according to claim 1, wherein $R_1$ is hydrogen or methyl; $R_2$ is $C_2$-$C_6$alkylene; $R_3$ is a group of the formula (II) with $R_1$ and $R_2$ being as defined above; and w is 2, 3 or 4, and, when w is 2, A is piperazine-1,4-diyl or a group of the formula (IVb) in which $R_9$ and $R_{11}$ which can be identical or different are hydrogen, methyl, 2,2,6,6-tetramethyl-4-piperidyl or 1,2,2,6,6-pentamethyl-4-piperidyl; $R_{10}$ is $C_2$-$C_6$alkylene, methylenedicyclohexylene or $C_4$-$C_{12}$alkylene interrupted by 1 or 2 groups

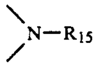

where $R_{15}$ is hydrogen, methyl or ($C_2$-$C_4$alkoxy)carbonyl; and when w is 3, A is a group of the formula (VIa) in which $R_{19}$ and $R_{22}$ which can be identical or different are hydrogen or methyl; $R_{20}$ is $C_2$-$C_6$alkylene or $C_4$-$C_6$alkylene interrupted by a group

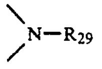

with $R_{29}$ being as defined above for $R_{15}$; and $R_{21}$ is $C_2$-$C_6$alkylene; and, when w is 4, A is a group of the formula (VII) where $R_{30}$ and $R_{33}$ which can be identical or different are hydrogen or methyl; $R_{31}$ and $R_{32}$ independently of one another are $C_2$-$C_3$alkylene; and x is 1.

8. A compound of the formula

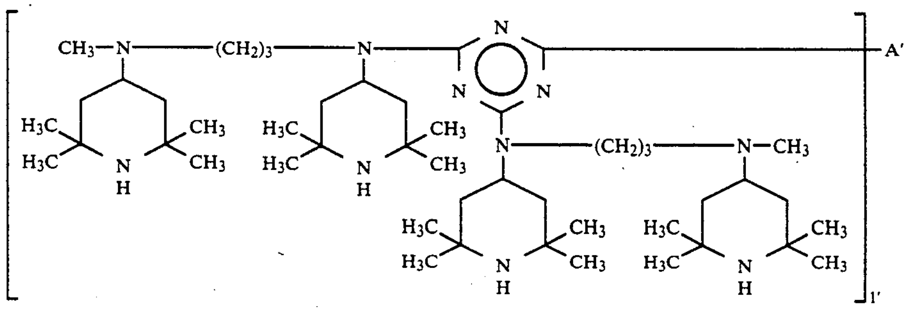

wherein 1' is 2 or 3 and when 1' is 2, A' is a group

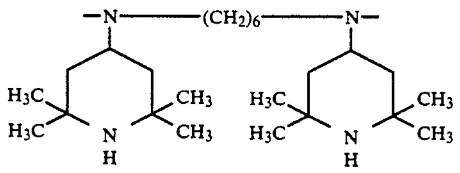

and when 1' is 3, A' is a group

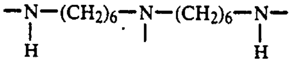

or

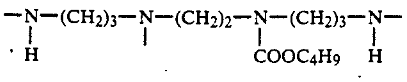

and a compound of the formula

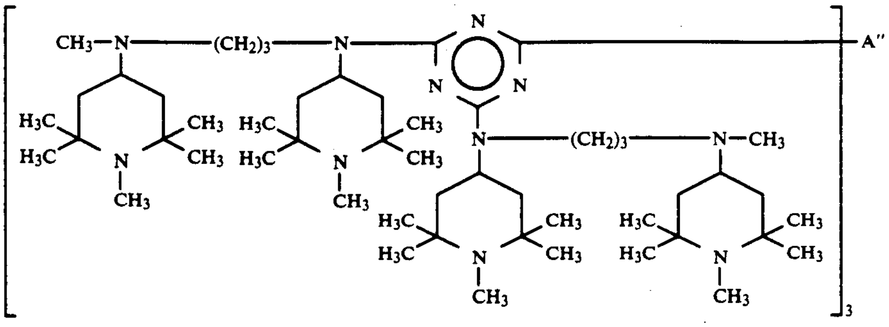
wherein A" is a group
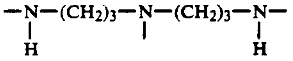
-continued
or
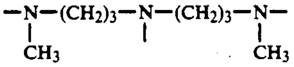
according to claim 1.
* * * * *